United States Patent [19]

Schiff et al.

[11] Patent Number: 5,722,953
[45] Date of Patent: Mar. 3, 1998

[54] NOZZLE ASSEMBLY FOR INJECTION DEVICE

[75] Inventors: David Schiff, Highland Park, N.J.; Paul Mulhauser, New York, N.Y.

[73] Assignee: Medi-Ject Corporation, Minneapolis, Minn.

[21] Appl. No.: 609,138

[22] Filed: Feb. 29, 1996

[51] Int. Cl.$^6$ .................................................. A61M 5/30
[52] U.S. Cl. .................................................. 604/68; 604/70
[58] Field of Search ........................... 604/68, 70, 71, 604/51, 135

[56] References Cited

U.S. PATENT DOCUMENTS

| | | |
|---|---|---|
| D. 304,616 | 11/1989 | Dunlap et al. |
| D. 349,958 | 8/1994 | Hollis et al. |
| 396,107 | 1/1889 | Nickerson . |
| 489,757 | 1/1893 | Reilly . |
| 1,567,517 | 12/1925 | Kisbey . |
| 1,973,706 | 9/1934 | Hawley . |
| 2,322,244 | 6/1943 | Lockhart . |
| 2,322,245 | 6/1943 | Lockhart . |
| 2,380,534 | 7/1945 | Lockhart . |
| 2,390,246 | 12/1945 | Folkman . |
| 2,398,544 | 4/1946 | Lockhart . |
| 2,413,303 | 12/1946 | Folkman . |
| 2,459,875 | 1/1949 | Folkman . |
| 2,547,099 | 4/1951 | Smoot . |
| 2,605,763 | 8/1952 | Smoot . |
| 2,635,602 | 4/1953 | Hein . |
| 2,653,602 | 9/1953 | Smoot . |
| 2,670,121 | 2/1954 | Scherer et al. |
| 2,671,347 | 3/1954 | Scherer . |
| 2,681,653 | 6/1954 | Kuhne . |
| 2,688,968 | 9/1954 | Scherer . |
| 2,699,166 | 1/1955 | Dickinson, Jr. et al. |
| 2,704,542 | 3/1955 | Scherer . |
| 2,704,543 | 3/1955 | Scherer . |
| 2,705,953 | 4/1955 | Potez . |
| 2,714,887 | 8/1955 | Venditty . |
| 2,717,597 | 9/1955 | Hein, Jr. . |
| 2,737,946 | 3/1956 | Hein, Jr. . |
| 2,754,818 | 7/1956 | Scherer . |
| 2,762,369 | 9/1956 | Venditty . |
| 2,762,370 | 9/1956 | Venditty . |
| 2,764,977 | 10/1956 | Ferguson . |
| 2,789,839 | 4/1957 | Siebert . |
| 2,798,485 | 7/1957 | Hein, Jr. . |
| 2,798,486 | 7/1957 | Hein, Jr. . |
| 2,800,903 | 7/1957 | Smoot . |

(List continued on next page.)

FOREIGN PATENT DOCUMENTS

| | | |
|---|---|---|
| 2028870 | 5/1991 | Canada . |
| 2071115 | 12/1992 | Canada . |
| 0 157 906 | 10/1985 | European Pat. Off. . |
| 0 460 961 | 6/1991 | European Pat. Off. . |
| 2 254 153 | 5/1974 | Germany . |
| 959397 | 6/1964 | United Kingdom . |
| 2249159 | 2/1991 | United Kingdom . |
| WO 93/03779 | 3/1993 | WIPO . |
| WO 95/03844 | 2/1995 | WIPO . |
| WO 96/21482 | 7/1996 | WIPO . |

OTHER PUBLICATIONS

Catalog: Hoechst Celanese—Advanced Materials Group, "Vectra® Liquid Crystal Polymer".
Catalog: Industrial Gas Springs, Ltd.

*Primary Examiner*—Michael Buiz
*Assistant Examiner*—Julian W. Woo
*Attorney, Agent, or Firm*—Pennie & Edmonds LLP

[57] ABSTRACT

A nozzle assembly adapted for a fluid injector having a ram, includes a plunger assembly having first and second driving members. The first and second driving members are apart according to a predetermined first distance. The second driving member is spaced apart from the ram according to a predetermined second distance. The first and second distances are resiliently maintained by a resilient spring member operatively disposed between the two driving members. One of the first and second distances is selected to be the smallest and thereby controls the maximum pressure at which fluid is expelled from the nozzle assembly.

21 Claims, 4 Drawing Sheets

U.S. PATENT DOCUMENTS

| | | | |
|---|---|---|---|
| 2,816,543 | 12/1957 | Venditty et al. | |
| 2,816,544 | 12/1957 | Scherer et al. | |
| 2,820,655 | 1/1958 | Hileman . | |
| 2,821,193 | 1/1958 | Ziherl et al. | |
| 2,821,981 | 2/1958 | Ziherl et al. | |
| 2,825,332 | 3/1958 | Johnson . | |
| 2,902,994 | 9/1959 | Scherer . | |
| 2,921,582 | 1/1960 | Sadd . | |
| 2,928,390 | 3/1960 | Venditty et al. | |
| 3,057,349 | 10/1962 | Ismach . | |
| 3,066,670 | 12/1962 | Stauffer . | |
| 3,115,133 | 12/1963 | Morando . | |
| 3,123,070 | 3/1964 | Kath . | |
| 3,129,708 | 4/1964 | Krantz . | |
| 3,130,723 | 4/1964 | Venditty et al. | |
| 3,131,692 | 5/1964 | Love . | |
| 3,138,157 | 6/1964 | Ziherl et al. | |
| 3,140,713 | 7/1964 | Ismach . | |
| 3,147,967 | 9/1964 | Bougeard . | |
| 3,167,071 | 1/1965 | Venditty . | |
| 3,189,029 | 6/1965 | Stephens . | |
| 3,202,151 | 8/1965 | Kath . | |
| 3,245,703 | 4/1966 | Manly . | |
| 3,292,622 | 12/1966 | Banker . | |
| 3,308,818 | 3/1967 | Rutkowski . | |
| 3,330,276 | 7/1967 | Gordon . | |
| 3,330,277 | 7/1967 | Gabriels . | |
| 3,335,722 | 8/1967 | Lowry et al. | |
| 3,353,537 | 11/1967 | Knox et al. | |
| 3,406,684 | 10/1968 | Tsujino . | |
| 3,424,154 | 1/1969 | Kinsley . | |
| 3,461,867 | 8/1969 | Zimmet et al. | |
| 3,476,110 | 11/1969 | Yahner . | |
| 3,490,451 | 1/1970 | Yahner . | |
| 3,507,276 | 4/1970 | Burgess . | |
| 3,518,990 | 7/1970 | Banker . | |
| 3,521,633 | 7/1970 | Yahner . | |
| 3,526,225 | 9/1970 | Isobe . | |
| 3,527,212 | 9/1970 | Clark . | |
| 3,557,784 | 1/1971 | Shields . | |
| 3,561,443 | 2/1971 | Banker . | |
| 3,625,208 | 12/1971 | Frost et al. | |
| 3,659,587 | 5/1972 | Baldwin . | |
| 3,688,765 | 9/1972 | Gasaway . | |
| 3,714,943 | 2/1973 | Yanof et al. | |
| 3,768,472 | 10/1973 | Hodosh et al. | |
| 3,779,371 | 12/1973 | Rovinski . | |
| 3,782,380 | 1/1974 | Van Der Gaast . | |
| 3,783,895 | 1/1974 | Weichselbaum . | |
| 3,788,315 | 1/1974 | Laurens . | |
| 3,805,783 | 4/1974 | Ismach . | |
| 3,827,601 | 8/1974 | Magrath et al. | |
| 3,838,689 | 10/1974 | Cohen . | |
| 3,908,651 | 9/1975 | Fudge . | |
| 3,938,520 | 2/1976 | Scislowicz et al. | |
| 3,945,379 | 3/1976 | Pritz et al. | |
| 3,945,383 | 3/1976 | Bennett et al. | |
| 4,026,212 | 5/1977 | Dardick | 102/39 |
| 4,059,107 | 11/1977 | Iriguchi et al. | |
| 4,089,334 | 5/1978 | Schwebel et al. | |
| 4,141,675 | 2/1979 | O'Neill | 417/214 |
| 4,328,802 | 5/1982 | Curley et al. | |
| 4,387,879 | 6/1983 | Tauschinski . | |
| 4,421,508 | 12/1983 | Cohen . | |
| 4,447,225 | 5/1984 | Taff et al. | |
| 4,500,075 | 2/1985 | Tsuchiya et al. | |
| 4,505,709 | 3/1985 | Froning et al. | |
| 4,507,113 | 3/1985 | Dunlap . | |
| 4,518,385 | 5/1985 | Lindmayer et al. | |
| 4,561,856 | 12/1985 | Cochran . | |
| 4,588,403 | 5/1986 | Weiss et al. | |
| 4,596,556 | 6/1986 | Morrow et al. | |
| 4,619,651 | 10/1986 | Kopfer et al. | |
| 4,623,332 | 11/1986 | Lindmayer et al. | |
| 4,626,242 | 12/1986 | Fejes et al. | |
| 4,662,878 | 5/1987 | Lindmayer . | |
| 4,675,020 | 6/1987 | McPhee . | |
| 4,680,027 | 7/1987 | Parsons et al. | |
| 4,709,686 | 12/1987 | Taylor et al. | |
| 4,722,728 | 2/1988 | Dixon . | |
| 4,744,786 | 5/1988 | Hooven . | |
| 4,768,568 | 9/1988 | Fournier et al. | |
| 4,771,758 | 9/1988 | Taylor et al. | |
| 4,775,173 | 10/1988 | Sauer . | |
| 4,790,824 | 12/1988 | Morrow et al. | |
| 4,834,149 | 5/1989 | Fournier et al. | |
| 4,850,967 | 7/1989 | Cosmai . | |
| 4,863,427 | 9/1989 | Cocchi . | |
| 4,874,367 | 10/1989 | Edwards . | |
| 4,883,483 | 11/1989 | Lindmayer . | |
| 4,909,488 | 3/1990 | Seibert et al. | |
| 4,923,072 | 5/1990 | Rilliet . | |
| 4,940,460 | 7/1990 | Casey et al. | |
| 4,941,880 | 7/1990 | Burns . | |
| 4,948,104 | 8/1990 | Wirges . | |
| 4,950,240 | 8/1990 | Greenwood et al. | 604/110 |
| 4,989,905 | 2/1991 | Rajecki . | |
| 5,024,656 | 6/1991 | Gasaway et al. | |
| 5,031,266 | 7/1991 | Tilman et al. | |
| 5,041,715 | 8/1991 | Muller . | |
| 5,061,263 | 10/1991 | Yamazaki et al. | |
| 5,062,830 | 11/1991 | Dunlap . | |
| 5,064,413 | 11/1991 | McKinnon et al. | |
| 5,066,280 | 11/1991 | Braithwaite . | |
| 5,073,165 | 12/1991 | Edwards . | |
| 5,085,332 | 2/1992 | Gettig et al. | |
| 5,116,313 | 5/1992 | McGregor . | |
| 5,135,507 | 8/1992 | Haber et al. | |
| 5,161,786 | 11/1992 | Cohen . | |
| 5,165,560 | 11/1992 | Ennis, III et al. | |
| 5,176,406 | 1/1993 | Straghan . | |
| 5,181,912 | 1/1993 | Hammett | 604/110 |
| 5,188,599 | 2/1993 | Botich et al. | 604/110 |
| 5,190,523 | 3/1993 | Lindmayer . | |
| 5,193,517 | 3/1993 | Taylor et al. | |
| 5,209,362 | 5/1993 | Lutzker . | |
| 5,224,932 | 7/1993 | Lappas . | |
| 5,226,882 | 7/1993 | Bates . | |
| 5,281,202 | 1/1994 | Weber et al. | 604/132 |
| 5,292,308 | 3/1994 | Ryan . | |
| 5,304,128 | 4/1994 | Haber et al. | |
| 5,312,335 | 5/1994 | McKinnon et al. | |
| 5,312,577 | 5/1994 | Peterson et al. | |
| 5,316,198 | 5/1994 | Fuchs et al. | |
| 5,334,144 | 8/1994 | Alchas et al. | |
| 5,352,203 | 10/1994 | Vallelunga et al. | 604/110 |
| 5,356,380 | 10/1994 | Hoekwater et al. | |
| 5,360,146 | 11/1994 | Ikushima . | |
| 5,383,851 | 1/1995 | McKinnon, Jr. et al. | |
| 5,399,163 | 3/1995 | Peterson et al. | |
| 5,407,431 | 4/1995 | Botich et al. | |
| 5,413,471 | 5/1995 | Yamauchi | 425/129.1 |
| 5,423,756 | 6/1995 | Van der Merwe . | |
| 5,480,381 | 1/1996 | Weston | 604/68 |
| 5,499,972 | 3/1996 | Parsons | 604/68 |
| 5,569,189 | 10/1996 | Parsons | 604/68 |

NOZZLE ASSEMBLY FOR INJECTION DEVICE

TECHNICAL FIELD

The present invention relates to a fluid injector nozzle assembly having a plunger assembly coupled to a ram of an injecting device having a first member separated from a second member by a predetermined distance by a resilient biasing member, such as a spring.

BACKGROUND OF THE INVENTION

Medical communities have become concerned over the possibility of accidental communication of disease, such as Acquired Immune Deficiency Syndrome (AIDS), hepatitis, and other diseases communicable through bodily fluids, through accidental needle sticking and improperly sterilized multiple-use needle injectors. One way to curb some of these mishaps is to employ a needleless injecting device.

Needleless injectors have no needle. They thus completely remove any apprehension or the possibility of being pierced by a contaminated needle. At least in this regard, the needleless injectors are superior in eliminating accidental disease transmission. Different needleless injector types have been contemplated, as described, for instance, in U.S. Pat. Nos. 5,062,830 issued to Dunlap; 4,790,824 to Morrow et al.; 4,623,332 to Lindmayer et al.; 4,421,508 to Cohen; 4,089,334 to Schwebel et al.; 3,688,765 to Gasaway; 3,115,133 to Morando; 2,816,543 to Venditty et al.; and 2,754,818 to Scherer. These injectors have been contemplated to administer medication as a fine, high velocity jet, delivered under sufficient pressure to enable the jet to pass through the skin tissue without requiring a hypodermic needle. These injectors typically have a nozzle assembly which has a barrel-like nozzle body for holding medication therein. The nozzle member has an orifice through which a jet stream of medication is forced out from the chamber when a plunger/piston is fired or actuated by some type of energy source.

As disclosed in Dunlap, one method for improving the peak pressure of the jet stream is provide a predetermined gap between the plunger of the nozzle assembly and the ram of the energy source. However, there remains a need for a nozzle assembly which is capable of easily establishing and maintaining this predetermined gap after liquid medicine or the like has been drawn into the chamber and during the process of bleeding air from the chamber, prior to firing the injector.

SUMMARY OF THE INVENTION

The present invention relates to a nozzle assembly adapted for use with an injector device. The nozzle assembly comprises a fluid chamber, a plunger assembly, including a resilient biasing member, preferably in the form of a spring. The chamber includes first and second ends with an orifice at the first end for passage of the fluid and being open at the second end. The plunger assembly is movably received in the chamber for expelling fluid out of or drawing fluid into the chamber by moving the plunger assembly relative to the chamber. The plunger assembly includes first and second driving members operatively connected to each other for expelling out and/or drawing in fluid, with the second driving member being spaced apart from the first driving member by a preselected first gap. The resilient spring is disposed between the first and second driving members for resiliently maintaining the gap. When a force sufficient to compress the spring is applied to the second driving member in a direction toward the second driving member, the second driving member moves across the gap toward the first driving member for urging the first driving member towards the chamber orifice to expel fluid therefrom.

Advantageously, the first and second driving members are operatively connected by a sleeve member and the spring is disposed within the sleeve members between the driving members. Preferably, the second driving member has a seal in contact with an inner wall of the chamber to prevent fluid from exiting the chamber around the second driving member and through the open end. Also, the chamber includes a connector adapted for connecting the nozzle to the injector, and it may include external ridges or threads for connection to an injection device.

If desired, the first driving member may include an end post or other coupling means such as flextabs, which can be grasped to move the first driving member in a direction away from the chamber orifice to draw fluid into the chamber. Subsequent movement in the opposite direction can bleed or purge air or excess fluid from the chamber before firing the injector. To assist in the movement of fluid, the chamber may include a tapered portion adjacent the orifice and the first driving member may include a tapered end portion which conforms to the tapered portion of the chamber.

BRIEF DESCRIPTION OF THE DRAWINGS

A better understanding of the invention may be obtained from a review of the appended drawing figures, which illustrate preferred embodiments and wherein.

DETAILED DESCRIPTION OF THE PREFERRED EMBODIMENTS

Figures 1, 2:
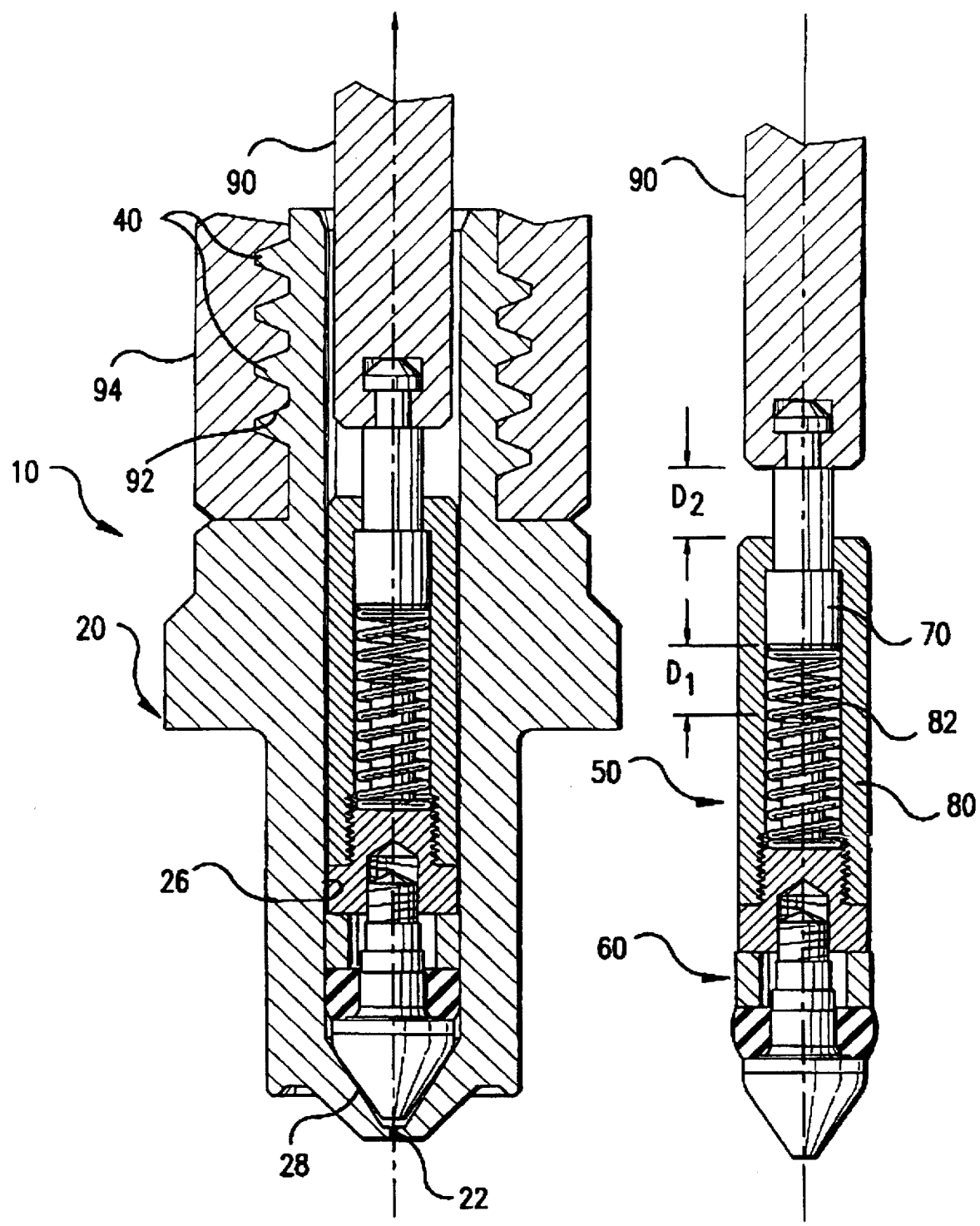
FIG. 1 is a partial cross-sectional view of a nozzle assembly according to the present invention adapted to be connected to an injector only partially shown.
FIG. 2 is a partial cross-sectional view of a plunger assembly according to the present invention adapted to be connected to a ram only partially shown.
Figure 3:
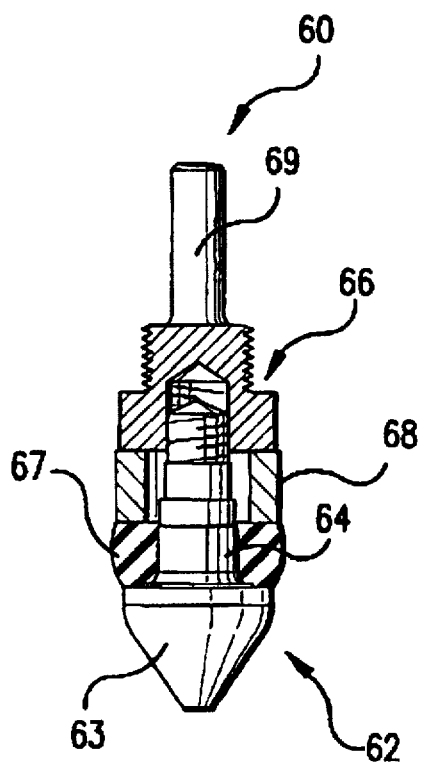
FIG. 3 is a partial cross-sectional view of a tip member of the plunger assembly shown in FIG. 2.
Figure 4:
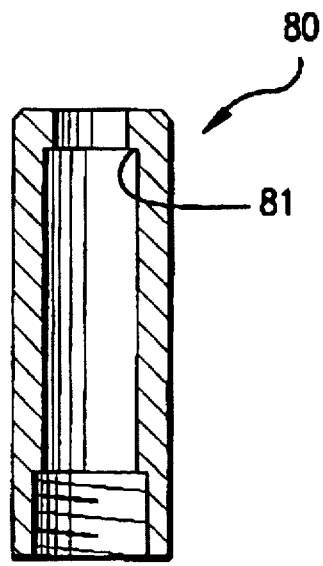
FIG. 4 is a cross-sectional view of the sleeve member of the plunger assembly shown in FIG. 2.
Figure 5:
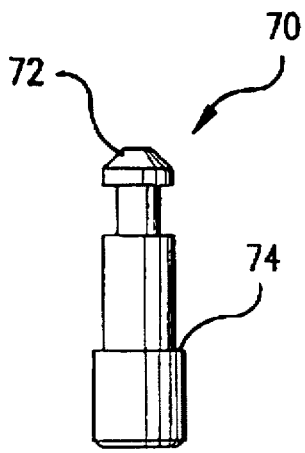
FIG. 5 is an external view of a pin member of the plunger assembly shown in FIG. 2.

The nozzle assembly 10 according to the present invention is adapted for use with any conventional injector, including the needleless type disclosed in the aforementioned patents, the disclosure of which is incorporated herein by reference. When a needle-type injector is to be used, the orifice is in fluid communication with the bore of an appropriately sized needle.

The assembly 10 has a nozzle member 20 having at least one orifice 22 of a suitable diameter that would produce a uniform jet stream under a given desired pressure range and depth of injection. Preferably for a single orifice, this diameter may be about 0.07–0.4 mm, and most preferably about 0.165 mm (0.0065 inches). If a highly precise jet stream is desired, the orifice can be formed of a synthetic gem material, such as a synthetic ruby or sapphire, as disclosed in U.S. Pat. No. 4,722,728 to Dixon. Hereinafter, the term "orifice" shall mean any type of opening, including a straight, convergent, divergent, convergent-divergent, etc.

As used in this application, the terms "proximal" or "proximally" shall denote an end or direction toward orifice 22, and the terms "distal" or "distally" shall mean an end or direction longitudinally away from the orifice 22.

The orifice may also be used to draw a fluid or liquid selected from medication or the like into the chamber. In this regard, a medication filling device such as an adapter for filling the internal chamber of a nozzle assembly from a liquid medication supply vial directly through the ejection orifice can be used to fill the chamber with medication, as described in U.S. Pat. Nos. 4,507,113 to Dunlap; and 4,883,483 and 4,662,878 to Lindmayer, the disclosure of which is incorporated herein by reference. Other coupling devices can also be used if desired.

The nozzle member 20, as shown in FIGS. 1 and 6–9, includes a cylindrical ampule chamber 26 terminating in a tapered end portion. The chamber includes external helical threads 40 for selectively removable attachment to an injection device. The plunger assembly 50, as shown individually in FIG. 2, has a pressure wall contoured to the cone 28 and is received through an open end of the chamber 26. It is positioned to reciprocally move longitudinally within the ampule chamber 26 to expel fluid out of the chamber and may also draw fluid into the chamber.

As better shown in FIGS. 2–5, plunger assembly 50 comprises a tip member or first driving member 60, a pin member 70, a sleeve member 80, and a resilient spring member 82. These members have a generally cylindrical shape and are connected together as shown in FIG. 2. Preferably, the spring member 82 is a helical compression spring. Pin member 70 is inserted into sleeve member 80 until an external annular shoulder 74 of the pin member 70 comes into contact with an internal annular shoulder 81 of the sleeve member 80. The relative sizes and orientations of the shoulders 74, 81 help ensure that the pin member 70 is retained within the sleeve member 80. An end post 72 of the pin member 70 extends outside of sleeve member 80. Spring 82 is then inserted into sleeve member 80 as shown. Finally, tip member 60 is threadedly connected to sleeve member 80, and compresses spring member 82 to a point where a predetermined first distance $D_1$ or spacing between the distal end of tip member 62 and the proximal end of pin member 70 is resiliently maintained.

Tip member 60 comprises front member 62, which has a conical head or tapered pressure wall member 63, a connecting member 66, and a back member 66. Alternatively, the back member 64 may be integrally formed with the front member 62. A seal member 67 and adjacent backup ring 68 are disposed between front member 62 and back member 66. As shown in FIG. 1, seal member 67 is preferably an o-ring having an outer diameter which is slightly larger than the inner diameter of ampule member 26, so that plunger assembly 50 is in a slidingly sealing relationship with ampule member 26.

As shown, the connecting member 64 of front member 62 is threadedly connected to back member 66. In this configuration, when seal member 67 has to be replaced, front member 62 can be separated from back member 66 to expose seal member 67 for removal and replacement. Furthermore, back member 66 comprises tail member 69, which is received within spring member 82. As stated above, the distance between the distal end of tail member 69 and the proximal end of pin member 70 constitutes the first distance $D_1$. Conical member 63 is configured and dimensioned to fit within cone 28 so that when plunger assembly 50 is pushed against ampule chamber 26, substantially all the fluid is expelled from ampule chamber 26.

Preferably, the plunger assembly 50 is made out of a plastic, such as polycarbonate or polypropylene, or a more durable material such as aluminum, stainless steel, or other metal. As described above, members of the plunger assembly 50 can be easily separated for cleaning or replacement.

Referring to FIGS. 1 and 6–9, the nozzle assembly 10 is attached to an injector body by connecting the end post 72 of the pin member 70 to the ram 90 of the injector, and connecting the external helical threads 40 to the complementary internal helical threads 92 defined in a front portion of the injector body 94. The connection between the plunger assembly and the ram 90 can be any conventional connection that holds these elements together but enables separation, such as a ball and slot configuration as depicted. The distal end of the sleeve member 80 and the proximal end of the ram 90 are spaced apart according to a predetermined second distance $D_2$ which is preferably selected to be smaller than the first distance $D_1$. Thus, the second distance $D_2$ constitutes the controlled gap or free travel distance that the ram 90 travels before impacting or otherwise moving the distal end of the sleeve member 80. In this embodiment, the sleeve member 80 functions as a second driving member. The relatively large surface area of the annular distal end of the sleeve member 80 advantageously accommodates the impact loading by the ram 90 and resists wear from repeated use of the injector.

Figure 6:
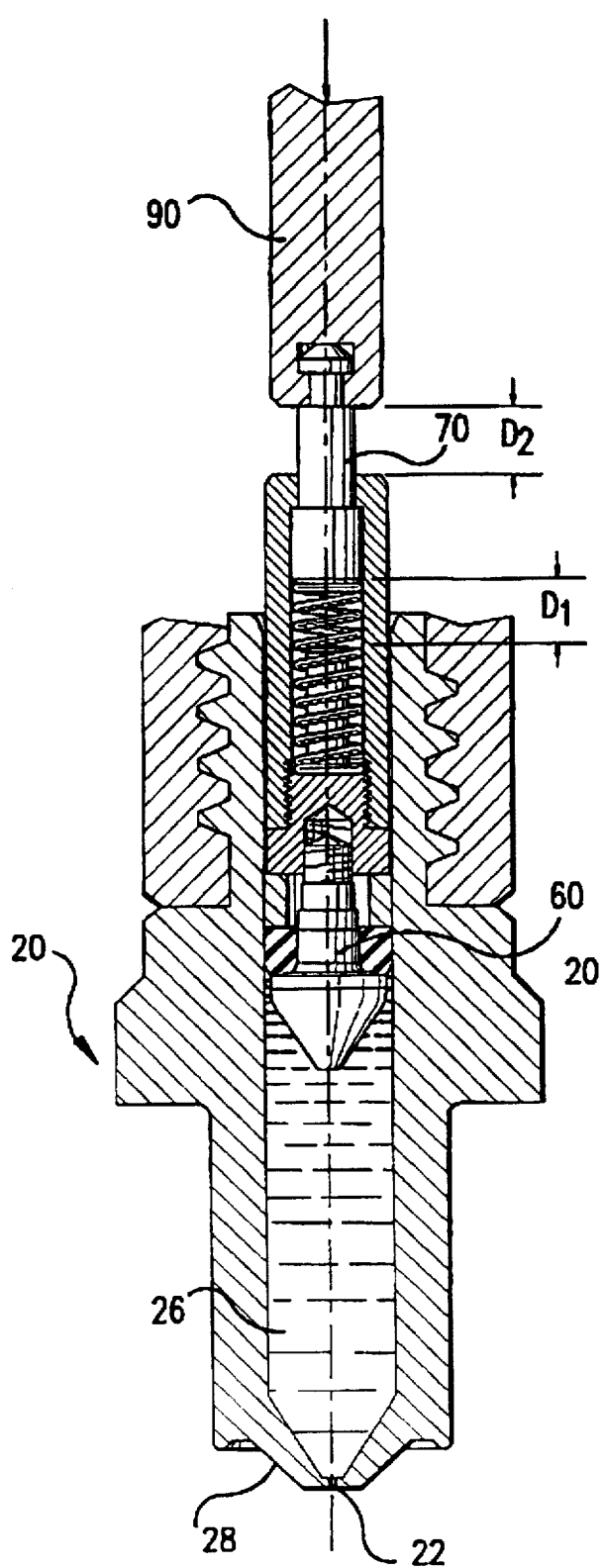
FIG. 6 is a partial cross-sectional view of the nozzle assembly of the present invention after drawing fluid into a chamber.
Figure 7:
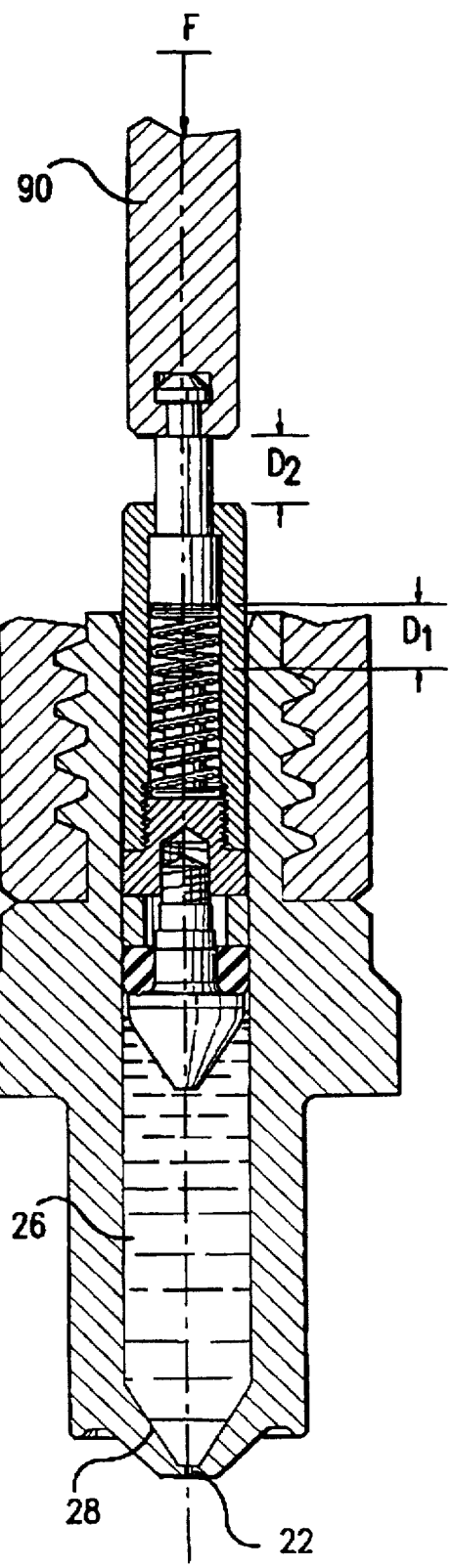
FIG. 7 is a partial cross-sectional view of the nozzle assembly of the present invention ejecting air and/or excess fluid out of the chamber.

The plunger assembly 50 is pushed proximally into the ampule chamber 26, to purge air. FIG. 1 shows the plunger assembly fully pushed, before the desired injection fluid is drawn into the chamber. As the plunger assembly is pulled distally, a partial vacuum is established inside the chamber 26 and the desired fluid is drawn into the chamber via the orifice 22, as depicted in FIG. 6.

In the event that air bubbles and/or excess fluid are drawn into ampule chamber 26, the plunger assembly must be pushed distally to expel the bubbles or excess fluid. As shown from FIGS. 6 and 7, and according to a preferred embodiment of the present invention, spring member 82 has sufficient stiffness to resist relative movement between pin member 70 and tip member 60. And since spring member 82 is pre-loaded (being compressed within sleeve member 80), the gap $D_2$ or free travel distance between the ram 90 and sleeve member 80 is maintained. It is within the ordinary skill of the art worker to select a proper resilient spring member to accomplish this purpose. Once installed, the preload on the spring member 82 provides a force greater than the force required to move the plunger assembly 50 within the chamber 26 and towards the orifice 22 for filling or purging prior to firing the injector.

Figure 8:
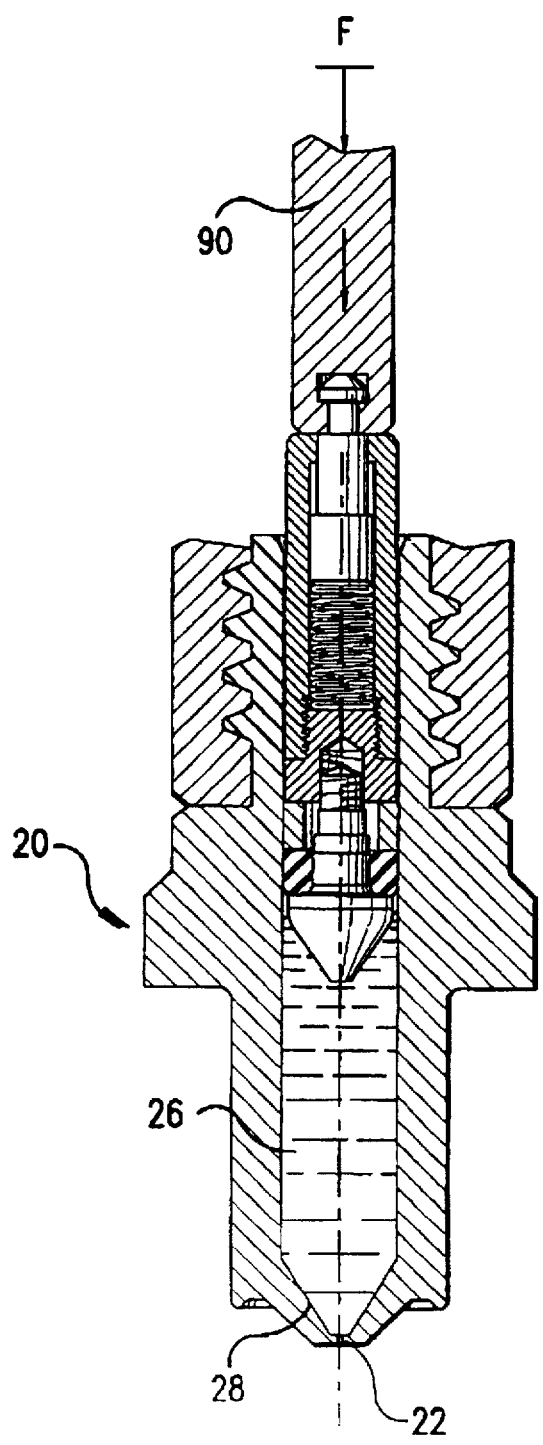
FIG. 8 is a partial cross-sectional view of the nozzle assembly of the present invention after the energy device has been activated and the ram has travelled across a predetermined gap.
Figure 9:
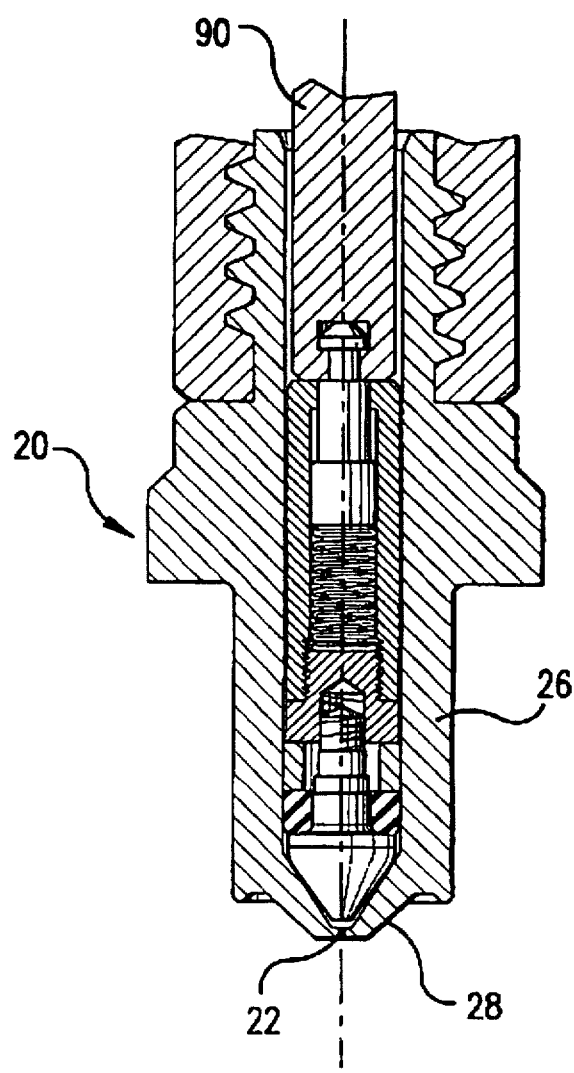
FIG. 9 is a partial cross-sectional view of the nozzle assembly of the present invention after the plunger has pushed the fluid out of the chamber.

Upon an application of a relatively large injection force F from the injecting device on the ram 90, the ram transmits this force F to the pin member 70. This force F compresses resilient spring member 82 and allows the ram 90 to travel across the gap $D_2$ and directly transmit the force to the sleeve member 80 thereby proximally moving the sleeve member 80 and tip member 60 to eject fluid out of the chamber 26, as shown in FIGS. 8-9. If the nozzle assembly 10 is to be reused by the same patient, the pin member 70 is pulled distally by the ram 90 as depicted in FIG. 6 and, due to the resiliency of the spring member 82, the first and second distances $D_1$, $D_2$ are accurately reestablished or restored.

After fluid injection is completed, the nozzle assembly 10 can be rotated until the threads 40 are free of the corresponding threads 92 on the injector body 94 so that the nozzle assembly 10 can be removed for cleaning and/or replacement of the pin member 70.

In a normal operation of a needleless injector, ram 90 of the injection device is operatively connected to an energy source and imparts a sudden force or impact F to the pin member, which force is high enough to compress spring 82 and to allow the ram 90 to directly drive the sleeve member 80 and tip member 60 towards the orifice 22. This action is sufficient to drive the fluid contained in ampule chamber 26 outward through orifice 22 at a relatively high peak jet stream pressure of, for example, in excess of 5,000 psi. By "high pressure", what is meant is a jet stream pressure which is capable of penetrating the skin of a patient. This would be a pressure of greater than 1,000 psi and typically between about 3,000 and 10,000 psi.

The second distance or gap $D_2$ plays an important role in creating the preferred pressure spike necessary to pierce through the patient's skin or other portion of the patient's body. Changing the magnitude of the gap $D_2$ will change the initial force imparted on the tip member 60. The peak pressure thus can be varied by varying the gap $D_2$. It can also vary depending upon the viscosity of the fluid to be injected, the desired injection penetration depth and other parameters which may affect the initial injection pressure output. One of ordinary skill in the art can determine by routine experimentation the optimum gap for any plunger assembly that is to be used with a particular injection fluid. Advantageously, pin 70, tip 60, plunger assembly 50 or nozzle assembly 10 or any combination of the above can be manufactured with different indicia such as different color codes and/or other markings, wherein each different indicia denotes a resulting predetermined length of gap $D_2$. This indicia coding scheme will easily assist the user in choosing a proper nozzle assembly for a specific application.

Also, in another embodiment, the first distance $D_1$ between the distal end of the tip member 60 and the proximal end of the pin member 70 is chosen to be less than the second distance $D_2$. In this arrangement, the pin member 70 functions as the second driving member wherein the proximal end of pin member 70 thrusts into the distal end of tip member 60, when the ram 90 and pin member 70 compress the spring member 82.

The nozzle assembly 10 can be connected to an injection device using any known structure for attaching and detaching two components together. The present invention preferably contemplates a bayonet mount, which has diametrically opposed threads 40. These threads 40 are first aligned in an opening having a similar cross-sectional configuration provided in an injector so that the threads can be inserted. Thereafter, the nozzle member 20 is rotated relative to the injector body by a predetermined degree to prevent the nozzle body from detaching in the axial direction. The bayonet-mount enables a quick attachment and detachment of the nozzle assembly. Other connection means can be used, if desired for a particular application.

It should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A nozzle assembly adapted for use with an injector device comprising:
   a chamber for holding a fluid and having first and second ends with an orifice at the first end for passage of the fluid and being open at the second end;
   a plunger movably received in said chamber for expelling fluid out of or drawing fluid into the chamber by moving the plunger relative to the chamber, the plunger comprising first and second driving members operatively connected to each other for expelling out and drawing in fluid, with the first driving member being spaced apart from the second driving member by a preselected gap; and
   a resilient biasing member disposed between the first and second driving members for resiliently maintaining said gap.

2. The nozzle assembly according to claim 1, wherein, when a force sufficient to compress said biasing member is applied between the first and second driving members, the first driving member moves across said gap toward the second driving member for urging the second driving member towards the chamber orifice to expel fluid therefrom.

3. The nozzle assembly according to claim 1, wherein said resilient biasing member is a spring.

4. The nozzle assembly according to claim 3, wherein said first and second driving members are operatively connected by a sleeve member and said spring is disposed within the sleeve members between the driving members.

5. The nozzle assembly according to claim 1, wherein the second driving member has a seal in contact with an inner wall of the chamber to prevent fluid from exiting the chamber around the second driving member and through the open end.

6. The nozzle assembly according to claim 1, wherein the chamber includes a connector adapted for connecting the nozzle to the injector.

7. The nozzle assembly of claim 1, wherein the first driving member includes an end post which can be grasped to move the first driving member in a direction away from the chamber orifice to either draw fluid into the chamber.

8. The nozzle assembly of claim 1, wherein the chamber includes a tapered portion adjacent the orifice and the second driving member includes a tapered cone which conforms to the tapered portion of the chamber.

9. The nozzle assembly of claim 1, wherein the chamber includes external threads for connection to an injection device.

10. The nozzle assembly of claim 1, wherein the second driving member includes specific indicia indicating a corresponding resultant predetermined length of said gap when the nozzle assembly is installed in the injector.

11. The nozzle assembly of claim 10, wherein said indicia includes a specific color code, selected from different color codes, corresponding to a respective predetermined length of said gap.

12. The nozzle assembly of claim 1, further including specific indicia marked on the nozzle assembly indicating a corresponding resultant predetermined length of said gap when the nozzle assembly is connected to the injector.

13. A nozzle assembly adapted for a needleless hypodermic fluid injector having a ram and a nozzle member defining a blind bore and at least one orifice communicating with said bore, said nozzle assembly comprising;

- a plunger assembly adapted to be movably positioned within said bore, said bore and movable plunger assembly collectively defining a variable-volume fluid chamber communicating with said orifice, said plunger assembly adapted to be selectively movable by the ram between a first position at which the fluid chamber has a minimum volume, a second position at which the fluid chamber has a maximum volume, and an intermediate position at which the fluid chamber has an intermediate volume smaller than the maximum volume and greater than the minimum volume; and
- a resilient spring having a preselected preload, said spring operative for maintaining a free travel distance between the ram and the plunger assembly when a force sufficient to move the plunger assembly but less than said preload is applied to the plunger assembly.

14. The nozzle assembly of claim 13, wherein said resilient spring is operative to collapse the free travel distance when a force sufficient to move the plunger assembly and greater than said preload is applied to the plunger assembly.

15. The nozzle assembly of claim 13, wherein said spring is adapted to be operatively positioned between the plunger assembly and the ram.

16. The nozzle assembly of claim 15, wherein said plunger assembly includes a tip member, a sleeve member, and a pin member operatively connected to each other for selectively drawing fluid into the chamber via the orifice and expelling fluid from the chamber via the orifice, said sleeve member defining another bore, said pin member adapted to be removably connected to the ram and extending into said another bore, said resilient spring positioned in the another bore and adapted to bias the sleeve member away from the ram according to the free travel distance.

17. The nozzle assembly of claim 16, wherein said another bore of the sleeve member defines an internal shoulder adapted to face away from the ram, said pin member including an external shoulder contacting said internal shoulder when the plunger assembly is at its second position, said resilient spring biasing the pin member apart from the tip member according to another distance greater than said free travel distance.

18. The nozzle assembly of claim 16, wherein said pin member includes a reduced diameter tail portion extending from said external shoulder and adapted to engage the ram, said tail portion having a selected length between its external shoulder and the ram, said free travel distance being a function of the selected length of the tail portion.

19. The nozzle assembly of claim 18, wherein said pin member includes indicia means for indicating a resulting free travel distance when the pin member is installed in said nozzle assembly.

20. The nozzle assembly of claim 13, wherein said plunger assembly further includes a seal member, said tip member defining a circumferential groove, said seal member positioned in said groove and sealedly contacting said bore of the nozzle member.

21. A needleless hypodermic fluid injector having a moveable ram, comprising:

- an injector body;
- a nozzle member removably connected to the injector body, said nozzle member defining a blind bore and at least one orifice communicating with said bore;
- a movable plunger assembly positioned within said bore, said bore and plunger assembly collectively defining a variable-volume fluid chamber communicating with said orifice, said plunger assembly being selectively movable by the ram between a first position at which the fluid chamber has a minimum volume, a second position at which the fluid chamber has a maximum volume, and an intermediate position at which the fluid chamber has an intermediate volume smaller than the maximum volume and greater than the minimum volume; and
- a resilient spring having a preselected preload and being operative for maintaining a free travel distance between the ram and the plunger assembly when a force sufficient to move the plunger assembly but less than said preload is applied to the plunger assembly.

\* \* \* \* \*